United States Patent
DeFossa et al.

(10) Patent No.: US 8,163,774 B2
(45) Date of Patent: *Apr. 24, 2012

(54) AMIDE-SUBSTITUTED 8-N-BENZIMIDAZOLES, METHOD FOR THE PRODUCTION THEREOF, AND USE OF THE SAME AS MEDICAMENTS

(75) Inventors: Elisabeth DeFossa, Idstein (DE); Karl Schoenafinger, Alzenau (DE); Gerhard Jaehne, Frankfurt (DE); Christian Buning, Bonn (DE); Georg Tschank, Essenheim (DE); Ulrich Werner, Miehlen (DE)

(73) Assignee: Sanofi-Aventis, Paris (FR)

( * ) Notice: Subject to any disclaimer, the term of this patent is extended or adjusted under 35 U.S.C. 154(b) by 1068 days.

This patent is subject to a terminal disclaimer.

(21) Appl. No.: 11/854,578

(22) Filed: Sep. 13, 2007

(65) Prior Publication Data

US 2008/0090868 A1     Apr. 17, 2008

Related U.S. Application Data

(63) Continuation of application No. PCT/EP2006/002058, filed on Mar. 7, 2006.

(30) Foreign Application Priority Data

Mar. 19, 2005 (DE) .......... 10 2005 012 874

(51) Int. Cl.
*A61K 31/445* (2006.01)
*C07D 401/00* (2006.01)

(52) U.S. Cl. ...................... 514/322; 546/199
(58) Field of Classification Search .......... 514/322; 546/199

See application file for complete search history.

(56) References Cited

U.S. PATENT DOCUMENTS 6,025,372 A * 2/2000 Yang et al. ............ 514/316
7,728,026 B2 * 6/2010 Zhu et al. ............. 514/394

FOREIGN PATENT DOCUMENTS

| EP | 1069124 | 1/2001 |
|----|---------|--------|
| WO | WO 02/48152 | 6/2002 |
| WO | WO 03/104233 | 12/2003 |
| WO | WO2004096793 | * 11/2004 |
| WO | WO2007/069053 | * 6/2007 |

OTHER PUBLICATIONS

Sitagliptin Wikipedia p. 1-3 (2010).*
Baradi et al. "Novel 8-heterocycl . . . " Exp. Opin.Drg. Dis. 2(9) 1161-1183 (2007).*
Gupta et al. "Emerging drug . . . " Cur. Drug. target 10, 71-87 (2009).*
McIntosh et al. "application of DPP IV . . . " Int. J. Biochem. Cell Biol. 38, p. 860-872 (2006).*
Zhu et al. "preparation of 2-substituted" CA145:419145 (2006).*
Zhu et al. "Preparation of 2-substituted . . . " CA 145:419147 (2006).*
Jordan, V. C. Nature Reviews: Drug Discovery, 2, pp. 205-213 (2003).*
. Dorwald "Side Reactions in Organic Synthesis: A Guide to Successful Synthesis Design, Weinheim: Wiley-VCH Verlag GmbH & Co. KGaA,". Preface (2005).*
Goker "Synthesis of new . . . " Farmoco 53, p. 415-420 (1998).*

* cited by examiner

*Primary Examiner* — Celia Chang
(74) *Attorney, Agent, or Firm* — Scully, Scott, Murphy & Presser, P.C.

(57) ABSTRACT

The present invention comprises the use of amino-substituted 8-N-benzimidazoles compounds of formula I

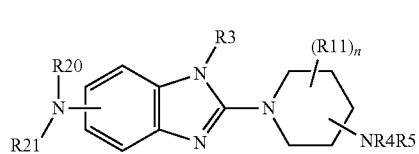

wherein R3, R4-R5, R11 and R20-R21 are hereinafter defined which display a therapeutically utilizable blood sugar-lowering action. These compounds are intended to be particularly suitable in the treatment of diabetes.

2 Claims, No Drawings

AMIDE-SUBSTITUTED 8-N-BENZIMIDAZOLES, METHOD FOR THE PRODUCTION THEREOF, AND USE OF THE SAME AS MEDICAMENTS

CROSS-REFERENCE TO RELATED APPLICATIONS

This application is a continuation of International Patent Application No. PCT/EP2006/002058 filed on Mar. 7, 2006 which is incorporated herein by reference in its entirety which claims the benefit of priority of German patent application Ser. No. 10/2005012874.2 filed on Mar. 19, 2005.

FIELD OF THE INVENTION

The present invention relates generally to pharmaceutical compounds and compositions comprising them for the treatment of metabolic blood serum disorders and the physiological manifestations thereof. More specifically, the present invention relates to pharmaceutical compounds and compositions comprising them for the treatment of metabolic blood glucose disorders such as diabetes, hypoglycemia, hyperglycemia, hyperlipidemia, hypercholesterolemia and the like. More specifically, the present invention relates to amino-substituted 8-N-benzimidazoles and derivatives thereof for the treatment of blood glucose disorders.

BACKGROUND OF THE INVENTION

The present invention comprises the use of amino-substituted 8-N-benzimidazoles and the physiologically compatible salts thereof for producing a pharmaceutical composition for the treatment of blood sugar disorders. These compounds are particularly useful in the reduction of blood sugar and, more specifically, in the therapeutic treatment of diabetes. The use of related or similar compounds has been known and described in the prior art as follows. EP 1069124 describes 2-benzimidazolylamines as ORL-1 receptor agonists. WO 97/12615 describes benzimidazole derivatives as 15-LO inhibitors and WO 02/04425 describes structurally similar virus polymerase inhibitors. WO 02/46168 describes benzimidazole derivatives for treating Alzheimer's disease.

SUMMARY OF THE INVENTION

The present invention comprises the use of amino-substituted 8-N-benzimidazoles compounds of formula I

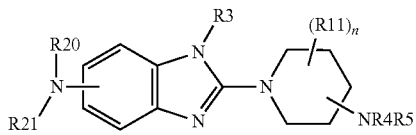

wherein R3, R4-R5, R11 and R20-R21 are hereinafter defined which display a therapeutically utilizable blood sugar-lowering action. These compounds are intended to be particularly suitable in the treatment of diabetes.

DETAILED DESCRIPTION OF THE INVENTION

The present invention relates to carboxamide derivative compounds of the formula I, below:

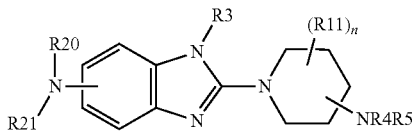

and their use in the treatment of blood sugar disorders wherein:

R20 is selected from the group consisting of H, $(C_1-C_3)$-alkyl, where $(C_1-C_3)$-alkyl is optionally mono- or polysubstituted by CN, $NO_2$, SH, OH, $(C_1-C_6)$-alkyl, O—$(C_1-C_6)$-alkyl or S—$(C_1-C_6)$-alkyl;
$(C_4-C_6)$-alkyl, where $(C_4-C_6)$-alkyl is optionally mono- or polysubstituted by F, Cl, Br, I, CN, $NO_2$, SH, OH, $CF_3$, $(C_1-C_6)$-alkyl, O—$(C_1-C_6)$-alkyl or S—$(C_1-C_6)$-alkyl; $(C_7-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-aryl $(C_1-C_6)$-alkylene-$(C_6-C_{10})$-heterocycle and $S(O)_2$-aryl, wherein the alkyl, cycloalkyl, alkenyl, alkynyl, alkylene, aryl and heterocycle groups are optionally mono- or polysubstituted by F, Cl, Br, I, CN, $NO_2$, SH, OH, $CF_3$, $(C_1-C_6)$-alkyl, O—$(C_1-C_6)$-alkyl or S—$(C_1-C_6)$-alkyl;
R21 is selected from the group consisting of $(C_1-C_3)$-alkyl, where $(C_1-C_3)$-alkyl is optionally mono- or polysubstituted by CN, $NO_2$, SH, OH, $(C_1-C_6)$-alkyl, O—$(C_1-C_6)$-alkyl or S—$(C_1-C_6)$-alkyl; $(C_4-C_6)$-alkyl, where $(C_4-C_6)$-alkyl is optionally mono- or polysubstituted by F, Cl, Br, I, CN, $NO_2$, SH, OH, $CF_3$, $(C_1-C_6)$-alkyl, O—$(C_1-C_6)$-alkyl or S—$(C_1-C_6)$-alkyl; $(C_7-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, where $(C_1-C_6)$-alkylene-$(C_6-C_{10})$-aryl $(C_1-C_6)$-alkylene-$(C_6-C_{10})$-heterocycle and $S(O)_2$-aryl, where the alkyl, cycloalkyl, alkenyl, alkynyl, alkylene, aryl and heterocycle radicals are optionally mono- or polysubstituted by F, Cl, Br, I, CN, $NO_2$, SH, OH, $CF_3$, $(C_1-C_6)$-alkyl, O—$(C_1-C_6)$-alkyl or S—$(C_1-C_6)$-alkyl;
excluding those definitions of the R21 substituent wherein it is unsubstituted phenyl or unsubstituted benzyl;
R3 is selected from the group consisting of $(C_1-C_6)$-alkyl, $(C_3-C_7)$-cycloalkyl, $(C_3-C_7)$-cycloalkyl-$(C_1-C_3)$-alkyl, phenyl and pyridyl, where the alkyl, cycloalkyl, cycloalkylalkyl, phenyl and pyridyl radicals are optionally mono- or polysubstituted by CN, $NO_2$, —$CF_3$, —$OCF_3$, OR12, NR7R8, NR7CONR7R8, COR7, OCOR7, OCOOR7, COOR7, CONR7R8 or OCONR7R8; $(C_2-C_{10})$-alkenyl, $(C_2-C_{10})$-alkynyl, $(C_6-C_{10})$-aryl, heterocycle and $(C_1-C_6)$-alkylene-$(C_6-C_{10})$-aryl, where the alkenyl, alkynyl, aryl, heterocycle and alkylenearyl radicals are optionally mono- or polysubstituted by F, Cl, Br, I, CN, $NO_2$, OH, $(C_1-C_6)$-alkyl, —$CF_3$, —$OCF_3$, OR7, NR7R8, NR7CONR7R8, COR7, OCOR7, OCOOR7, COOR7, CONR7R8 or OC(O)NR7R8;
excluding those definitions of R3 wherein it is an unsubstituted phenyl or unsubstituted pyridyl, or substituted phenyl or substituted pyridyl wherein each is substituted by F, Cl, Br, I, OH or $(C_1-C_6)$-alkyl, from the R3 substituent;

3

R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R12 is selected from the group consisting of $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_2-C_4)$-alkylene-$(C_6-C_{10})$-aryl and $(C_1-C_4)$-alkylene-heterocycle;

R4 and R5 are each independently selected from the group consisting of H, $(C_1-C_6)$-alkyl and $(C_3-C_8)$-cycloalkyl, where $(C_1-C_6)$-alkyl and $(C_3-C_8)$-cycloalkyl are optionally substituted by F, Cl, Br, I, CN, aryl, heterocycle, $NH_2$, $NH(C_1-C_6)$-alkyl, $N((C_1-C_6)$-alkyl$)_2$, OH, $O(C_1-C_6)$-alkyl, (O)aryl, (O)heteroaryl, $S(C_1-C_6)$-alkyl, $S(O)(C_1-C_6)$-alkyl and $S(O)_2(C_1-C_6)$-alkyl, wherein these alkyl groups may in turn be substituted by F, Cl, Br or I;

R11 is selected from the group consisting of H, F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, wherein the alkyl groups may be mono- or poly-substituted by F, Cl, Br or I;

n is 0, 1 or 2;

and the pharmaceutically acceptable salts thereof.

Preferably, the present invention comprises compounds of formula I in which one or more of the substituents are each defined as follows:

R20 is H;

R21 is selected from the group consisting of $(C_3-C_{10})$-cycloalkyl, $(C_1-C_6)$-alkylene-$(C_6-C_{10})$-aryl, phenyl, $(C_1-C_6)$-alkylene-$(C_6-C_{10})$-pyridyl, wherein the cycloalkyl, aryl and pyridyl radicals may be mono- or polysubstituted by F, Cl, Br, I, CN, $NO_2$, SH, OH, $CF_3$, $(C_1-C_6)$-alkyl, O—$(C_1-C_6)$-alkyl and S—$(C_1-C_6)$-alkyl;

excluding those definitions wherein R21 is an unsubstituted phenyl or unsubstituted benzyl;

R3 is selected from the group consisting of $(C_1-C_6)$-alkyl, $(C_3-C_7)$-cycloalkyl, $(C_3-C_7)$-cycloalkyl-$(C_1-C_3)$-alkyl, phenyl, pyridyl, where the alkyl, cycloalkyl, cycloalkylalkyl, phenyl and pyridyl radicals are mono- or polysubstituted by CN, $NO_2$, —$CF_3$, —$OCF_3$, OR12, NR7R8, NR7CONR7R8, COR7, OCOR7, OCOOR7, COOR7, CONR7R8 and OCONR7R8; $(C_2-C_{10})$-alkenyl, $(C_2-C_{10})$-alkynyl, $(C_6-C_{10})$-aryl, heterocycle and $(C_1-C_6)$-alkylene-$(C_6-C_{10})$-aryl, wherein the alkenyl, alkynyl, aryl, heterocycle and alkylene-aryl radicals may be mono- or polysubstituted by F, Cl, Br, I, CN, $NO_2$, OH, $(C_1-C_6)$-alkyl, —$CF_3$, —$OCF_3$, OR7, NR7R8, NR7CONR7R8, COR7, OCOR7, OCOOR7, COOR7, CONR7R8 or OCONR7R8;

excluding those definitions wherein R3 is an unsubstituted phenyl or an unsubstituted pyridyl, or a phenyl and pyridyl substituted by F, Cl, Br, I, OH or $(C_1-C_6)$-alkyl;

4

R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R12 is selected from the group consisting of $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_2-C_4)$-alkylene-$(C_6-C_{10})$-aryl or $(C_1-C_4)$-alkylene-heterocycle;

R4 and R5 are each independently selected from the group consisting of H, $(C_1-C_6)$-alkyl or $(C_3-C_8)$-cycloalkyl, where $(C_1-C_6)$-alkyl or $(C_3-C_8)$-cycloalkyl may be substituted by F, Cl, Br, I, CN, aryl, heterocycle, $NH_2$, $NH(C_1-C_6)$-alkyl, $N((C_1-C_6)$-alkyl$)_2$, OH, $O(C_1-C_6)$-alkyl, O-aryl, O-heteroaryl, $S(C_1-C_6)$-alkyl, $S(O)(C_1-C_6)$-alkyl or $S(O)_2(C_1-C_6)$-alkyl, where these alkyl groups may in turn be substituted by F, Cl, Br or I;

R11 is selected from the group consisting of H, F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, where the alkyl groups may be mono- or polysubstituted by F, Cl, Br or I;

n is 0, 1 or 2;

and the pharmaceutically acceptable salts thereof.

More preferably, the present invention comprises compounds of formula I in which one or more of the substituents are each more specifically defined as follows:

R20 is H;

R21 is selected from the group consisting of $(C_3-C_{10})$-cycloalkyl, $(C_1-C_6)$-alkylene-$(C_6-C_{10})$-aryl, phenyl, $(C_1-C_6)$-alkylene-$(C_6-C_{10})$-pyridyl, where the cycloalkyl, aryl and pyridyl radicals may be mono- or polysubstituted by F, Cl, Br, I, CN, $NO_2$, SH, OH, $CF_3$, $(C_1-C_6)$-alkyl, O—$(C_1-C_6)$-alkyl and S—$(C_1-C_6)$-alkyl;

excluding those definitions of R21 wherein it is an unsubstituted phenyl or unsubstituted benzyl;

R3 is independently selected from the group consisting of $(C_2-C_{10})$-alkenyl or $(C_1-C_6)$-alkylene-$(C_6-C_{10})$-aryl, where the alkenyl and $(C_1-C_6)$-alkylene-$(C_6-C_{10})$-aryl radicals may be mono- or polysubstituted by F, Cl, Br;

R4 and, R5 are each H;

n is 0;

and the pharmaceutically acceptable salts thereof.

Most preferably, the present invention comprises compounds of formula I in which one or more of the substituents are each more specifically defined as follows:

R20 is H;

R21 is $(C_3-C_{10})$-cycloalkyl, benzyl, pyridyl, phenyl, where the alkyl, cycloalkyl and benzyl radicals may be mono- or polysubstituted by F, Cl, Br, I, CN, $NO_2$, SH, OH, $(C_1-C_6)$-alkyl, O—$(C_1-C_6)$-alkyl and S—$(C_1-C_6)$-alkyl;

excluding the definitions of the R21 substituent wherein it is an unsubstituted phenyl and unsubstituted benzyl;

R3 is independently selected from the group consisting of
(C$_2$-C$_{10}$)-alkenyl or (C$_1$-C$_6$)-alkylene-(C$_6$-C$_{10}$)-aryl,
where the alkenyl and (C$_1$-C$_6$)-alkylene-(C$_6$-C$_{10}$)-aryl
radicals may be mono- or polysubstituted by F, Cl, Br;
R4, R5 are each H;
n is 0;
and the pharmaceutically acceptable salts thereof.

The present invention also comprises compounds of formula I in the form of their racemates, racemic mixtures, pure enantiomers, their diastereomers and mixtures thereof.

When the R-groups or substituents can occur more than once in the compounds of formula I, they may all each independently have the definitions specified and be the same or different.

Owing to their higher water solubility, pharmaceutically acceptable salts are particularly suitable for medical applications compared to the starting or base compounds. These salts must have a pharmaceutically acceptable anion or cation. Suitable pharmaceutically acceptable acid addition salts of the inventive compounds are salts of inorganic acids such as hydrochloric acid, hydrobromic acid, phosphoric acid, metaphosphoric acid, nitric acid and sulfuric acid, and organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1, 3-propanediol), diethanolamine, lysine or ethylenediamine.

Salts with a pharmaceutically unacceptable anion, for example trifluoroacetate, are likewise included in the scope of the invention as useful intermediates for the preparation or purification of pharmaceutically acceptable salts and/or for the use in non-therapeutic, for example in vitro, applications.

The term "physiologically functional derivative" used here refers to any physiologically compatible derivative of an inventive compound of the formula I, for example an ester which, on administration to a mammal, for example the human, is capable (directly or indirectly) of forming a compound of the formula I or an active metabolite thereof.

The physiologically functional derivatives also include prodrugs of the inventive compounds. Such prodrugs can be metabolized in vivo to give an inventive compound. These prodrugs may or may not themselves be active.

The inventive compounds may also be present in various polymorphic forms, for example as amorphous and crystalline polymorphic forms. All polymorphic forms of the inventive compounds are included within the scope of the invention and are a further aspect of the invention.

Hereinafter, all references to "compound(s) of the formula (I)" relate to compound(s) of the formula I as described above, and also their salts, solvates and physiologically functional derivatives as described herein.

An alkyl substituent means a straight-chain or branched hydrocarbon chain having one or more carbons, for example methyl, ethyl, isopropyl, tert-butyl, hexyl and so on.

The alkyl radicals may be mono- or poly-substituted by suitable groups, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle; PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$; C(=NH)(NH$_2$), NH$_2$, NH—(C$_1$-C$_6$)-alkyl, N((C$_1$-C$_6$)-alkyl)$_2$, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-COO—(C$_1$-C$_6$)-alkyl, N((C$_1$-C$_6$)-alkyl)-CO-aryl, N((C$_1$-C$_6$)-alkyl)-CO-heterocycle, N((C$_1$-C$_6$)-alkyl)-COO-aryl, N((C$_1$-C$_6$)-alkyl)-COO-heterocycle, N((C$_1$-C$_6$)-alkyl)-CO—NH—(C$_1$-C$_6$)-alkyl), N((C$_1$-C$_6$)-alkyl)-CO—NH-aryl, N((C$_1$-C$_6$)-alkyl)-CO—NH-heterocycle, N((C$_1$-C$_6$)-alkyl)-CO—N((C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N((C$_1$-C$_6$)-alkyl)$_2$, N(heterocycle)-CO—N((C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, where n may be 0-6, where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

An alkenyl substituent means a straight-chain or branched hydrocarbon chain having two or more carbons and one or more double bonds, for example vinyl, allyl, pentenyl, 2-methyl-but-2-en-4-yl.

The alkenyl substituent may be mono- or polysubstituted by suitable groups, for example:
F, Cl, Br, I, CF$_3$, NO$_2$, N$_3$, CN, COOH, COO(C$_1$-C$_6$)alkyl, CONH$_2$, CONH(C$_1$-C$_6$)alkyl, CON [(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle; PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$; C(=NH)(NH$_2$), NH$_2$, NH—(C$_1$-C$_6$)-alkyl, N((C$_1$-C$_6$)-alkyl)$_2$, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-

COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

An alkynyl substituent means a straight-chain or branched hydrocarbon chain having two or more carbons and one or more triple bonds, for example ethynyl, propynyl, butynyl, hexynyl.

The alkynyl radicals may be mono- or polysubstituted by suitable groups, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, $SO_2$—N(($CH_2$)$_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

An aryl substituent is a phenyl, naphthyl, biphenyl, tetrahydronaphthyl, alpha- or beta-tetralonyl, indanyl or indan-1-onyl radical.

The aryl substituents may be mono- or polysubstituted by suitable groups, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_r$-aryl, $SO_2$—NH($CH_2$)$_r$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_r$-aryl)$_2$, $SO_2$—N(($CH_2$)$_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

A cycloalkyl substituent means a ring system which comprises one or more rings and is present in saturated or partially unsaturated form (with one or two double bonds), and is formed exclusively from carbon atoms, for example cyclopropyl, cyclopentyl, cyclopentenyl, cyclohexyl or adamantyl.

The cycloalkyl radicals may be mono- or polysubstituted by suitable groups, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—N(($C_1$-$C_6$)-alkyl)$(CH_2)_n$-aryl, $SO_2$—N(($C_1$-$C_6$)-alkyl)$(CH_2)_n$-heterocycle, $SO_2$—N($(CH_2)_n$-aryl)$_2$, $SO_2$—N($(CH_2)_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$; C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

Heterocycle substituents or groups or "heterocyclic substituent ring systems mean those groups which, apart from carbon, also contain heteroatoms, for example nitrogen, oxygen or sulfur. This definition also includes ring systems in which the heterocycle or the heterocyclic radical is fused to benzene rings. The heterocycle or the heterocyclic group may be aromatic, saturated aliphatic or partially unsaturated aliphatic.

Suitable heterocycle substituents or "heterocyclic groups" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is 2-, 3- or 4-pyridyl. Thienyl is 2- or 3-thienyl. Furyl is 2- or 3-furyl.

Also included are the corresponding N-oxides of these compounds, i.e., for example, 1-oxy-2-, -3- or -4-pyridyl.

Also included are mono- or polybenzo fused derivatives of these heterocyclic groups.

The heterocyclic rings or heterocyclic radicals may be mono- or polysubstituted by suitable groups, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—N(($C_1$-$C_6$)-alkyl)$(CH_2)_n$-aryl, $SO_2$—N(($C_1$-$C_6$)-alkyl)$(CH_2)_n$-heterocycle, $SO_2$—N($(CH_2)_n$-aryl)$_2$, $SO_2$—N($(CH_2)_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$; C(=NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)- alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, where n may be 0-6, where the aryl group or heterocyclic group may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

The compound(s) of the formula (I) may also be administered in combination with additional active ingredients.

The amount of a compound of the formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 mg, typically from 1 ng to 10 mg, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of the formula I may be used for therapy of the afore-mentioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of the formula I. The inventive pharmaceutical compositions may be produced by one of the known pharmaceutical methods which consist essentially in mixing the constituents with pharmacologically acceptable carriers and/or excipients.

The pharmaceutical compositions of the present invention are those which are suitable for oral, rectal, topical, peroral (for example sublingual) and parenteral (for example subcutaneous, intra-muscular, intra-dermal or intra-venous) administration, although the most suitable mode of administration depends in each individual case on the nature and severity of the condition to be treated and on the type of the compound of the formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of the formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration include preferably sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa butter, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986).

The compounds of the formula I may be administered alone or else also in combination with one or more additional active ingredients. Other useful active ingredients for combination products are as follows:

One or more anti-diabetic compounds disclosed in the Rote Liste 2001, chapter 12 may also be incorporated as a second additional active in the compositions of the present invention. They can be combined with the inventive compounds of the formula I, in particular for synergistic enhancement of action.

The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Anti-diabetics include insulin and insulin derivatives, for example Lantus® (see www.lantus.com) or Apidra®, fast-acting insulins (see U.S. Pat. No. 6,221,633), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells (PPAR=peroxisome proliferator-activated receptor, PXR=pregnane X receptor, ATP=adenosine triphosphate).

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin (HMG-CoA=3-hydroxy-3-methylglutaryl coenzyme A).

In one embodiment of the invention, the compounds of the formula I are administered in combination with a cholesterol absorption inhibitor, for example, ezetimibe, tiqueside, pamaqueside, or with a compound as described in PCT/EP 2004/00269, WO 2004/000804, WO 2004/000803, WO 2004/000805, EP 0114531, U.S. Pat. No. 6,498,156.

In one embodiment of the invention, the compounds of the formula I are administered in combination with a PPAR gamma agonist, for example, rosiglitazone, pioglitazone, JTT-501, GI 262570.

In one embodiment of the invention, the compounds of the formula I are administered in combination with PPAR alpha agonist, for example, GW 9578, GW 7647.

In one embodiment of the invention, the compounds of the formula I are administered in combination with a mixed PPAR alpha/gamma agonist, for example, GW 1536, AVE 8042, AVE 8134, AVE 0847, or as described in WO 00/64888, WO 00/64876, DE10142734.4.

In one embodiment of the invention, the compounds of the formula I are administered in combination with a fibrate, for example fenofibrate, clofibrate, bezafibrate.

In one embodiment of the invention, the compounds of the formula I are administered in combination with an MTP inhibitor, for example implitapide, BMS-201038, R-103757 (MTP=microsomal triglyceride transfer protein).

In one embodiment of the invention, the compounds of the formula I are administered in combination with bile acid absorption inhibitor (see, for example, U.S. Pat. No. 6,245,744 or U.S. Pat. No. 6,221,897), for example HMR 1741.

In one embodiment of the invention, the compounds of the formula I are administered in combination with a CETP inhibitor, for example JTT-705 (CETP=cholesteryl ester transfer protein).

In one embodiment of the invention, the compounds of the formula I are administered in combination with a polymeric bile acid adsorber, for example cholestyramine, colesevelam.

In one embodiment of the invention, the compounds of the formula I are administered in combination with an LDL receptor inducer (see U.S. Pat. No. 6,342,512), for example HMR1171, HMR1586 (LDL=low density lipids).

In one embodiment of the invention, the compounds of the formula I are administered in combination with an ACAT inhibitor, for example avasimibe (ACAT=acyl coenzyme A: cholesterol acyl transferase).

In one embodiment of the invention, the compounds of the formula I are administered in combination with an antioxidant, for example OPC-14117.

In one embodiment of the invention, the compounds of the formula I are administered in combination with a lipoprotein lipase inhibitor, for example NO-1886.

In one embodiment of the invention, the compounds of the formula I are administered in combination with an ATP citrate lyase inhibitor, for example SB-204990.

In one embodiment of the invention, the compounds of the formula I are administered in combination with a squalene synthetase inhibitor, for example BMS-188494.

In one embodiment of the invention, the compounds of the formula I are administered in combination with a lipoprotein (a) antagonist, for example CI-1027 or nicotinic acid.

In one embodiment of the invention, the compounds of the formula I are administered in combination with a lipase inhibitor, for example orlistat.

In one embodiment of the invention, the compounds of the formula I are administered in combination with insulin.

In one embodiment, the compounds of the formula I are administered in combination with a sulfonylurea, for example tolbutamide, glibenclamide, glipizide or glimepiride.

In one embodiment, the compounds of the formula I are administered in combination with a biguanide, for example metformin.

In yet another embodiment, the compounds of the formula I are administered in combination with a meglitinide, for example repaglinide.

In one embodiment, the compounds of the formula I are administered in combination with a thiazolidinedione, for example troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, for example miglitol or acarbose.

In one embodiment, the compounds of the formula I are administered in combination with adenosine A1 agonists, for example those which are described in WO 2004/003002.

In one embodiment, the compounds of the formula I are administered in combination with an active ingredient which acts on the ATP-dependent potassium channel of the beta cells, for example tolbutamide, glibenclamide, glipizide, glimepiride or repaglinide. In one embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists (NPY=neuropeptide Y), e.g. naphthalene-1-sulfonic acid {4-[(4-aminoquinazolin-2-ylamino)methyl] cyclohexylmethyl}amide hydrochloride (CGP 71683A)), MC4 agonists (MC4=melanocortin 4 receptor, e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (H3=histamine receptor, e.g. 3-cyclohexyl-1-(4,4-dimethyl-1,4,6,7-tetrahydroimidazo[4,5-c]pyridin-5-yl)propan-1-one oxalic acid salt (WO 00/63208)); TNF agonists (TNF=tumor necrosis factor), CRF antagonists (CRF=corticotropin releasing factor, e.g. [2-methyl-9-(2,4,6-trimethylphenyl)-9H-1,3,9-triazafluoren-4-yl]dipropylamine (WO 00/66585)), CRF BP antagonists (CRF BP=corticotropin releasing factor binding protein, e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients specified in WO 02/28346), MSH (melanocyte-stimulating hormone) agonists, CCK-A (CCK-A=cholecystokinin-A) agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists (serotonin mimetics) e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tert-butyl ester (WO 01/85695)), TRH agonists (TRH=TSH releasing hormone; TSH=thyroid-stimulating hormone; thyrotropin), see, for example, EP 0 462 884, uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (DA=dopamine autoreceptor, for example bromocriptine, doprexin), lipase/amylase inhibitors (e.g. WO 00/40569), PPAR modulators (e.g. WO 00/78312), RXR(RXR=retinoid X receptor) modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In yet another embodiment, the other active ingredient is sibutramine.

In one embodiment, the other active ingredient is orlistat.

In one embodiment, the other active ingredient is mazindol or phentermine.

In another embodiment, the other active ingredient is rimonabant.

In one embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230-6.); Caromax is a carob-containing product supplied by Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of foodstuffs, for example, in bakery products or muesli bars.

It will be appreciated that any suitable combination of the compounds according to the invention with one or more of the abovementioned compounds and optionally one or more further pharmacologically active substances is regarded as being covered by the scope of protection of the present invention.

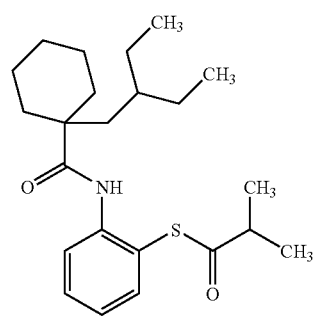

JTT-705

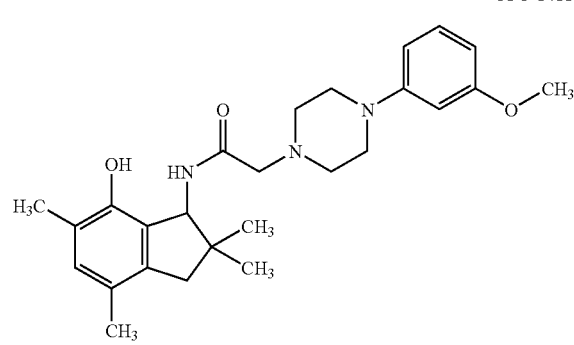

OPC-14117

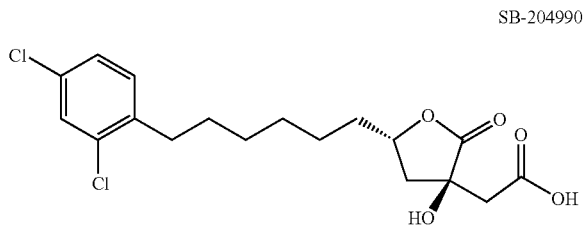

SB-204990

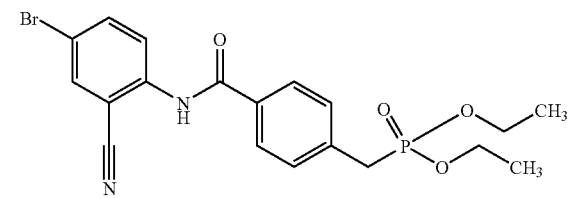

NO-1886

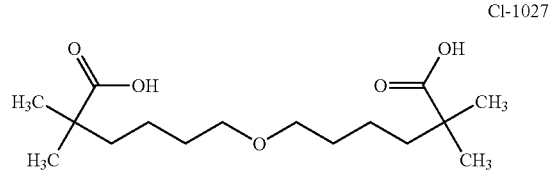

CI-1027

-continued

BMS-188494

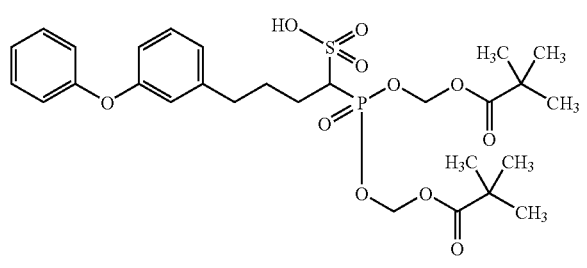

GI 262570

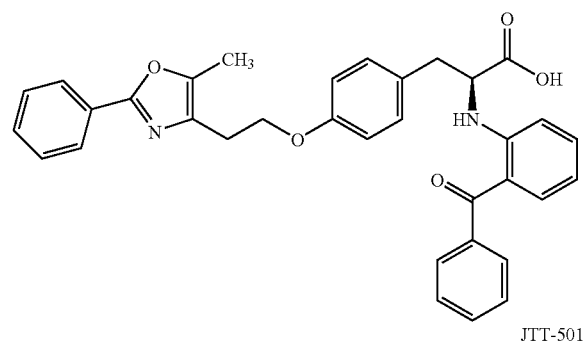

JTT-501

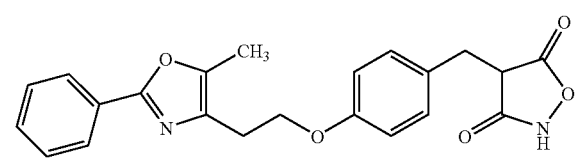

The compounds of formula I of the present invention can be prepared by reacting suitable starting materials of the formula II in which X is a leaving group, such as chlorine, bromine, iodine, sulfonyloxy, sulfinyl or sulfoxyl, and R30 is an ester or an amide, with a compound of the formula IV optionally in the presence of suitable bases and in suitable solvents.

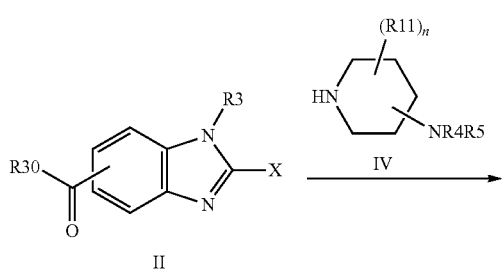

-continued

I

In the cases where R4 and R5 are simultaneously hydrogen, it may be appropriate to use the radical IV in a form protected on the nitrogen function and to detach the protecting group again on completion of reaction with 11. Such suitable protecting groups and the processes for their introduction and detachment are known (see: Theodora W. Greene and Peter G. M. Wuts, *Protective Groups in Organic Synthesis*, 3rd Edition, John Wiley & Sons, Inc., New York, 1999).

The halogen compounds of the formula II can be obtained by known processes, for example by halogenating the corresponding H, hydroxyl or thio compound (formula II, X=H, OH or SH). Suitable halogenating agents may, by way of example, be halogens such as chlorine and bromine, N-bromosuccinimide, phosphorus pentachloride or phosphorus oxychloride.

The synthesis of compounds of the formula II is described in the literature. They may be prepared, for example, by condensing substituted diaminobenzene derivatives with aldehydes in the presence of an oxidizing agent (for example atmospheric oxygen, oxygen, iodine, oxone, quinones, peroxides, etc.), or alternatively with carboxylic acids, nitrites or amides, without or in the presence of a catalyst.

The amines IV can be synthesized by processes known from the literature.

Some derivatives of the formula IV, for example piperidin-3-ylamines are commercially available.

The esters or amides CO—R30 can be converted to the amides CO—NR20R21 by methods known from the literature.

The tabulated examples listed below are provided to better illustrate methods for practicing the present invention as disclosed herein. The examples are provided to better describe and more specifically set forth the compounds, processes and methods of the present invention as contemplated herein. However, it is to be recognized that they are for illustrative purposes only, and should not be interpreted as limiting the spirit and scope of the invention as later recited by the claims that follow.

TABLE 1

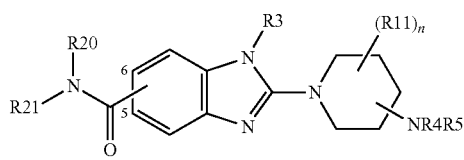

| Ex. | A No. | Binding site C=O— NR20R21 | R20 | R21 | R3 | NR4R5 | n | R11 |
|---|---|---|---|---|---|---|---|---|
| 1 | A003394 933A | 6 | H | 4-Cl-Benzyl- | 4-F-Benzyl | 3-R—NH$_2$ × HCl | 0 | — |

TABLE 1-continued

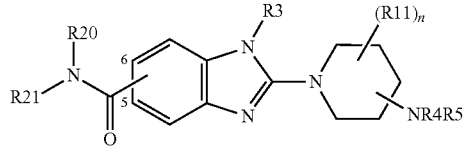

| Ex. | A No. | Binding site C=O— NR20R21 | R20 | R21 | R3 | NR4R5 | n | R11 |
|---|---|---|---|---|---|---|---|---|
| 2 | A003394934A | 6 | H | 3-CF$_3$-Benzyl- | 4-F-Benzyl | 3-R—NH$_2$ × HCl | 0 | — |
| 3 | A003394935A | 6 | H | 2-Cl-Benzyl- | 4-F-Benzyl | 3-R—NH$_2$ × HCl | 0 | — |
| 4 | A003394936A | 6 | H | Cyclohexyl- | 4-F-Benzyl | 3-R—NH$_2$ × HCl | 0 | — |
| 5 | A003394937A | 6 | H | 3-Pyridyl-CH$_2$— | 4-F-Benzyl | 3-R—NH$_2$ × HCl | 0 | — |
| 6 | A003395756A | 5 | H | 4-Cl-Benzyl- | 4-F-Benzyl | 3-R—NH$_2$ × HCl | 0 | — |
| 7 | A003395757A | 5 | H | 2-Cl-Benzyl- | 4-F-Benzyl | 3-R—NH$_2$ × HCl | 0 | — |
| 8 | A003395758A | 5 | H | 3-Pyridyl-(CH$_2$)$_2$— | 4-F-Benzyl | 3-R—NH$_2$ × HCl | 0 | — |
| 9 | A003395760A | 5 | H | 3-Cl-Benzyl- | 4-F-Benzyl | 3-R—NH$_2$ × HCl | 0 | — |
| 10 | A003401196A | 6 | H | Cyclopentyl- | —CH$_2$—CH=C(CH$_3$)$_2$ | 3-R—NH$_2$ × HCl | 0 | — |
| 11 | A003401273A | 6 | H | 4-F-Phenyl- | —CH$_2$—CH=C(CH$_3$)$_2$ | 3-R—NH$_2$ × HCl | 0 | — |
| 12 | A003401848A | 6 | H | 4-F-Phenyl- | 4-F-Benzyl | 3-R—NH$_2$ × HCl | 0 | — |

The compounds of formula I of the present invention feature favorable effects on lipid and carbohydrate metabolism; in particular, they lower the blood sugar level and are suitable for the treatment of type II diabetes, of insulin resistance, of dislipidemias and of metabolic syndrome/syndrome X. Moreover, the compounds are suitable for the treatment and prophylaxis of arteriosclerotic manifestations. The compounds can be used alone or in combination with further blood sugar-lowering active ingredients. The compounds act as DPP IV (dipeptidyl peptidase IV) inhibitors and are also suitable for the treatment of disorders of perception and other psychiatric indications, for example depressions, anxiety states, anxiety neuroses, schizophrenia, and for the treatment of disorders associated with the circadian rhythm, for weight reduction in mammals, for the treatment of immune disorders and for the treatment of drug abuse. They are additionally suitable for the treatment of cancer, arthritis, osteoarthritis, osteoporosis, sleep disorders, sleep apnea, masculine and feminine sexual disorders, inflammations, acne, pigmentation of the skin, disorders of steroid metabolism, skin diseases, psoriasis, mycoses, neurodegenerative disorders, multiple sclerosis and Alzheimer's disease.

The efficacy of the compounds was tested as follows:
Measurement of the DPP-IV activity:
Material:
DPP-IV from porcine kidneys (Sigma, Munich)
H-Ala-Pro-AFC (Bachem, Weil am Rhein)
Test conditions:
DPP-IV (1 mU/ml, end concentration)
H-Ala-Pro-AFC (15 µm end concentration)
in Tris/HCl (40 mM, pH 7.4), total volume 0.2 ml The reaction was performed at room temperature for different periods (typically 10 minutes) and stopped at the end of the reaction by adding 20 µl of ZnCl$_2$ (1 M). The conversion of H-Ala-Pro-AFC was determined fluorimetrically by measuring the emission at 535 nm on excitation at 405 nm. In the case of addition of inhibitors, the buffer volume added was adjusted such that a total volume of the test mixture of 200 µl was maintained.

IC$_{50}$ values for inhibitors were determined by varying the inhibitor concentrations at the given substrate concentration of 15 µM. K$_i$ and K$_m$ values were determined by corresponding variation of substrate and inhibitor concentration as described (Dixon, M. and Webb, E. C. (1979) Enzymes, third edition, pp. 47-206, Academic Press). The values for K$_m$, IC$_{50}$ and K$_i$ were calculated using a commercially available software package (Leatherbarrow, R. J. (1992) GraFit Version 3.0, Erithacus Software Ltd. Staines, U.K.).

TABLE 2

Biological activity of the examples:

| Example | IC$_{50}$ [µM] |
|---|---|
| 2 | 1.0 |
| 5 | 2.5 |
| 6 | 4.3 |
| 11 | 1.8 |

It can be seen from the table that the compounds of the formula I inhibit the activity of the DPP-IV (dipeptidyl peptidase IV) and are thus very suitable for lowering the blood sugar level.

The preparation of some working examples will be described in detail hereinafter; the other compounds of the formula I were obtained analogously:

Example 1

N-(4-Chlorobenzyl)-R-2-(3-aminopiperidin-1-yl)-1-(4-fluorobenzyl)-1H-benzimidazole-6-carboxamide hydrochloride a) Methyl 2-hydroxy-1H-benzimidazole-5-carboxylate

The solution of 5.9 g of carbonyldiimidazole in 10 ml of N-methylpyrrolidone is added dropwise to the solution of 5 g of methyl 3,4-diaminobenzoate in 10 ml of N-methylpyrrolidone, and the mixture is heated to 100° C. for 2 hours. After cooling to 60° C., 5 ml of methanol were added dropwise and then the mixture was stirred at room temperature with 150 ml of water, and the precipitate was filtered off with suction, washed with isopropanol and dried under reduced pressure.
Yield: 4.0 g m.p.: 312° C.

b) Methyl 2-chloro-1H-benzimidazole-5-carboxylate 3.9 g of methyl 2-hydroxy-1H-benzimidazole-5-carboxylate and 50 ml of phosphorus oxychloride are stirred at 10° C. for 6 hours. The resulting thick slurry is, after cooling, stirred cautiously into 500 ml of ice-water, and the solid is filtered off with suction after one hour, washed with water and dried under reduced pressure.
Yield: 4.3 g m.p.: 276° C.

c) Mixture of methyl 2-chloro-1-(4-fluorobenzyl)-1H-benzimidazole-6-carboxylate and methyl 2-chloro-1-(4-fluorobenzyl)-1H-benzimidazole-5-carboxylate 4.3 g of methyl 2-chloro-1H-benzimidazole-6-carboxylate are dissolved in 15 ml of N-methylpyrrolidone, admixed with 4.2 g of potash and stirred at room temperature for 60 minutes. 4.86 g of 4-fluorobenzyl bromide are then added and the mixture is stirred at 70° C. for 4 hours, cooled and stirred with 50 ml of water and 10 ml of glacial acetic acid. The solid is filtered off with suction and dried under reduced pressure.
Yield: 4.0 g m.p. resin d) Mixture of methyl R-2-(3-tert-butoxycarbonylaminopiperidin-1-yl)-1-(4-fluorobenzyl)-1H-benzimidazole-6-carboxylate and methyl 2-(3-tert-butoxycarbonylaminopiperidin-1-yl)-1-(4-fluorobenzyl)-1H-benzimidazole-5-carboxylate The mixture of methyl 2-chloro-1-(4-fluorobenzyl)-1H-benzimidazole-6-carboxylate and methyl 2-chloro-1-(4-fluorobenzyl)-1H-benzimidazole-5-carboxylate (2 g in total), 15 ml of N-methylpyrrolidone, 3 ml of triethylamine and 2.5 g of tert-butyl R-piperidin-3-ylcarbamate is heated to 100° C. for 6 hours. After being allowed to cool, the mixture is admixed with 50 ml of water and stirred. The liquid is decanted off from the semi-solid precipitate which is taken up again in 5 ml of methanol and precipitated again with 30 ml of water and stirred. The solid is filtered off with suction and dried under reduced pressure.
Yield: 2.1 g m.p.: resin e) R-2-(3-tert-Butoxycarbonylaminopiperidin-1-yl)-1-(4-fluorobenzyl)-1H-benzimidazole-6-carboxylic acid The mixture of a total of 2 g of R-2-(3-tert-butoxycarbonylaminopiperidin-1-yl)-1-(4-fluorobenzyl)-1H-benzimidazole-6-carboxylate and methyl R-2-(3-tert-butoxycarbonylaminopiperidin-1-yl)-1-(4-fluorobenzyl)-1H-benzimidazole-5-carboxylate in the solvent mixture of 10 ml of methanol, 20 ml of water and 10 ml of tetrahydrofuran is admixed with 500 mg of lithium hydroxide and stirred at room temperature for 24 hours. After adding 2 ml of glacial acetic acid, the volatile fractions were removed under reduced pressure, the residue was stirred with water, and the solid was filtered off with suction and then separated by column chromatography (silica gel, eluent: methylene chloride:isopropanol=94:6), the 5-isomer being eluted first.
Yield: 980 mg m.p.: resin f) tert-Butyl R-{1-[6-(4-chlorobenzylcarbamoyl)-1-(4-fluorobenzyl)-1H-benzimidazol-2-yl]-piperidin-3-yl}carbamate (F-34529-074)

The solution of 50 mg of R-2-(3-tert-butoxycarbonylaminopiperidin-1-yl)-1-(4-fluorobenzyl)-1H-benzimidazole-6-carboxylic acid in 1.5 ml of dimethylformamide was admixed successively with 40.6 mg of HATU, 18 μl of triethylamine and 14 μl of 4-chlorobenzylamine, and stirred at room temperature overnight. The mixture was then diluted with 5 ml of water and the precipitate was filtered off with suction and dried at 40° C. under reduced pressure.
Yield: 30 mg m.p.: resin g) N-(4-Chlorobenzyl)-R-2-(3-aminopiperidin-1-yl)-1-(4-fluorobenzyl)-1H-benzimidazole-6-carboxamide hydrochloride (F-34529-083)

The solution of 63 mg of tert-butyl R-{1-[6-(4-chlorobenzylcarbamoyl)-1-(4-fluorobenzyl)-1H-benzimidazol-2-yl]-piperidin-3-yl}carbamate in 1 ml of ethyl acetate is admixed with 0.2 ml of a saturated HCl solution in ethyl acetate and left to stand at room temperature overnight. The volatile fractions were removed on a rotary evaporator and the residue was dissolved in a little methylene chloride and precipitated with diisopropyl ether. The solid was filtered off with suction and dried at 40° C. under reduced pressure.
Yield: 15 mg m.p.: 197.1° C.

What is claimed is:
1. The compound of formula I

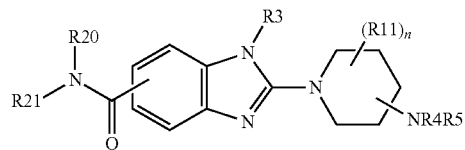

wherein
R20 is H;
R21 is selected from the group consisting of $(C_3-C_{10})$-cycloalkyl, $(C_1-C_6)$-alkylene-$(C_6-C_{10})$-aryl, phenyl and $(C_1-C_6)$-alkylene-$(C_6-C_{10})$-pyridyl, where the cycloalkyl, aryl and pyridyl radicals are optionally mono- or polysubstituted by F, Cl, Br, I, CN, $NO_2$, SH, OH, $CF_3$, $(C_1-C_6)$-alkyl, O—$(C_1-C_6)$-alkyl and S—$(C_1-C_6)$-alkyl;
excluding those definitions of R21 wherein it is an unsubstituted phenyl or unsubstituted benzyl;
R3 is selected from the group consisting of $(C_2-C_{10})$-alkenyl and $(C_1-C_6)$-alkylene-$(C_6-C_{10})$-aryl, where the alkenyl and $(C_1-C_6)$-alkylene-$(C_6-C_{10})$-aryl substituents are optionally mono- or poly-substituted by F, Cl, Br;
R4 and R5 are each H;

R11 is selected from the group consisting of H, F, Cl, Br, I, $(C_1$-$C_6)$-alkyl, $(C_3$-$C_8)$-cycloalkyl, $NH_2$, $NH(C_1$-$C_6)$-alkyl, $NH(C_3$-$C_7)$-cycloalkyl, $N((C_1$-$C_6)$-alkyl$)_2$ and O—$(C_1$-$C_6)$-alkyl, where the alkyl groups are optionally mono- or poly-substituted by F, Cl, Br or I; and n is 0;

or a pharmaceutically acceptable salt thereof.

2. The compound of formula I as recited in claim 1, wherein R20 is H;

R21 is $(C_3$-$C_{10})$-cycloalkyl, benzyl, pyridyl and phenyl, where the alkyl, cycloalkyl and benzyl radicals are optionally mono- or polysubstituted by F, Cl, Br, I, CN, $NO_2$, SH, OH, $(C_1$-$C_6)$-alkyl, O—$(C_1$-$C_6)$-alkyl or S—$(C_1$-$C_6)$-alkyl;

excluding the definitions of unsubstituted phenyl and unsubstituted benzyl from the R21 radical;

R3 is selected from the group consisting of $(C_2$-$C_{10})$-alkenyl and $(C_1$-$C_6)$-alkylene-$(C_6$-$C_{10})$-aryl, where the alkenyl and $(C_1$-$C_6)$-alkylene-$(C_6$-$C_{10})$-aryl radicals are optionally mono- or polysubstituted by F, Cl, Br;

R4 and R5 are each H;

R11 is selected from the group consisting of H, F, Cl, Br, I, $(C_1$-$C_6)$-alkyl, $(C_3$-$C_8)$-cycloalkyl, $NH_2$, $NH(C_1$-$C_6)$-alkyl, $NH(C_3$-$C_7)$-cycloalkyl, $N((C_1$-$C_6)$-alkyl$)_2$ and O—$(C_1$-$C_6)$-alkyl, where the alkyl groups are optionally mono- or poly-substituted by F, Cl, Br or I;

n is 0;

or a pharmaceutically acceptable salt thereof.

\* \* \* \* \*